(12) United States Patent
Yacobi et al.

(10) Patent No.: US 11,854,674 B2
(45) Date of Patent: Dec. 26, 2023

(54) DETERMINING RATE OF RECRUITMENT INFORMATION CONCERNING A CLINICAL TRIAL

(71) Applicant: Accenture Global Solutions Limited, Dublin (IE)

(72) Inventors: Ari Yacobi, Leander, TX (US); Mitchell Shuster, Doylestown, PA (US)

(73) Assignee: Accenture Global Solutions Limited, Dublin (IE)

(*) Notice: Subject to any disclaimer, the term of this patent is extended or adjusted under 35 U.S.C. 154(b) by 490 days.

(21) Appl. No.: 16/452,754

(22) Filed: Jun. 26, 2019

(65) Prior Publication Data

US 2020/0005908 A1 Jan. 2, 2020

Related U.S. Application Data

(60) Provisional application No. 62/693,343, filed on Jul. 2, 2018.

(51) Int. Cl.
*G16H 10/20* (2018.01)
*G06N 20/00* (2019.01)

(52) U.S. Cl.
CPC ............. *G16H 10/20* (2018.01); *G06N 20/00* (2019.01)

(58) Field of Classification Search
None
See application file for complete search history.

(56) References Cited

U.S. PATENT DOCUMENTS

| | | | |
|---|---|---|---|
| 8,370,280 B1 | 2/2013 | Lin et al. | |
| 2009/0292554 A1* | 11/2009 | Schultz | G06Q 10/06 705/2 |
| 2009/0313048 A1* | 12/2009 | Kahn | G16H 20/10 705/3 |
| 2014/0278469 A1* | 9/2014 | Secci | G16H 10/20 705/2 |
| 2016/0042155 A1* | 2/2016 | Li | G16H 10/20 705/2 |
| 2017/0061102 A1* | 3/2017 | Weber | G16H 10/60 |
| 2018/0046780 A1 | 2/2018 | Graiver et al. | |
| 2019/0354888 A1* | 11/2019 | Karvir | G06N 7/005 |

(Continued)

OTHER PUBLICATIONS

Anonymous., "Computer—Wikipedia, the free encyclopedia", Internet Archive Wayback Machine, Jul. 16, 2016, pp. 1-27, XP055640737, [retrieved on Nov. 8, 2019] Retrieved from the Internet [URL: https://web.archive.org/web/20160720112250/https://en.wikipedia.org/wiki/Computer].

(Continued)

*Primary Examiner* — Rajesh Khattar
*Assistant Examiner* — Andrew E Lee
(74) *Attorney, Agent, or Firm* — Harrity & Harrity, LLP

(57) ABSTRACT

A device may obtain identification information concerning a clinical trial, and may obtain, based on the identification information, selection information concerning the clinical trial and input information concerning the clinical trial. The device may select at least one machine learning model, of a plurality of machine learning models, based on the selection information, and may process, using the at least one machine learning model, the input information to determine predicted rate of recruitment (RoR) information concerning the clinical trial.

20 Claims, 8 Drawing Sheets

(56) References Cited

U.S. PATENT DOCUMENTS

2019/0355459 A1* 11/2019 Li .................. G16H 50/20
2019/0362838 A1* 11/2019 Srivastava ............ G16H 10/20

OTHER PUBLICATIONS

Extended European Search Report for Application No. EP19183750.9, dated Nov. 28, 2019, 13 pages.
Gajewski B.J., et al., "Predicting Accrual in Clinical Trials with Bayesian Posterior Predictive Distributions", Statistics in Medicine, vol. 27 (13), Nov. 2, 2007, pp. 2328-2340, XP055642113.
Katharine B.D., et al., "A Systematic Review of Models to Predict Recruitment to Multicentre Clinical Trials", Bmc Medical Research Methodology, Biomed Central, London, vol. 10 (1), Jul. 6, 2010, pp. 63, XP021073923.
Yadav R., et al., "EnForeSys -an Advanced Patient Enrollment Forecaster with Monte Carlo Simulations", PHUSE 2016, Oct. 12, 2016, 12 pages, XPG55641597.
Anonymous., "Bayesian Inference—Wikipedia," Jun. 2018, 12 pages, XP093016665, Retrieved from the Internet[URL: https://en.wikipedia.org/w/index.php?title=Bayesian_inference&oldid=846601106][retrieved on Jan. 23, 2023].

* cited by examiner

DETERMINING RATE OF RECRUITMENT INFORMATION CONCERNING A CLINICAL TRIAL

RELATED APPLICATION(S)

This application claims priority under 35 U.S.C. § 119 to U.S. Provisional Patent Application No. 62/693,343, filed on Jul. 2, 2018, the content of which is incorporated by reference herein in its entirety.

BACKGROUND

Rate of recruitment (RoR) is a metric used to measure recruitment of participants for a clinical trial. RoR may be related to a duration of the clinical trial and/or a number of sites associated with the clinical trial.

SUMMARY

According to some implementations, a method may include obtaining, by a device, identification information concerning a clinical trial. The method may include obtaining, based on the identification information, selection information concerning the clinical trial and input information concerning the clinical trial. The method may include selecting at least one machine learning model, of a plurality of machine learning models, based on the selection information, and processing, using the at least one machine learning model, the input information to determine predicted rate of recruitment (RoR) information concerning the clinical trial.

According to some implementations, a device may include one or more memories and one or more processors communicatively coupled to the one or more memories. The one or more processors may be configured to obtain identification information concerning a clinical trial from a first different device. The one or more processors may be configured to obtain, based on the identification information, selection information concerning the clinical trial and input information concerning the clinical trial from a second different device. The one or more processors may be configured to select at least one machine learning model, of a plurality of machine learning models, based on the identification information and the selection information, and process, using the at least one machine learning model, the input information to determine predicted rate of recruitment (RoR) information concerning the clinical trial.

According to some implementations, a non-transitory computer-readable medium may store one or more instructions. The one or more instructions, when executed by one or more processors of a device, may cause the one or more processors to obtain historical clinical trial information and historical rate of recruitment (RoR) information. The one or more instructions may cause the one or more processors to train a plurality of machine learning models based on the historical clinical trial information and the historical RoR information. The one or more instructions may cause the one or more processors to obtain identification information concerning a clinical trial, and obtain, based on the identification information, selection information concerning the clinical trial and input information concerning the clinical trial. The one or more instructions may cause the one or more processors to select at least one machine learning model, of the plurality of machine learning models, based on the selection information, and process, using the at least one machine learning model, the input information to determine predicted RoR information concerning the clinical trial. The one or more instructions may cause the one or more processors to obtain present RoR information concerning the clinical trial, determine a status of the clinical trial based on the present RoR information and the predicted RoR information, and cause, based on the determined status of the clinical trial, at least one action to be performed.

DETAILED DESCRIPTION

Figure 1A:
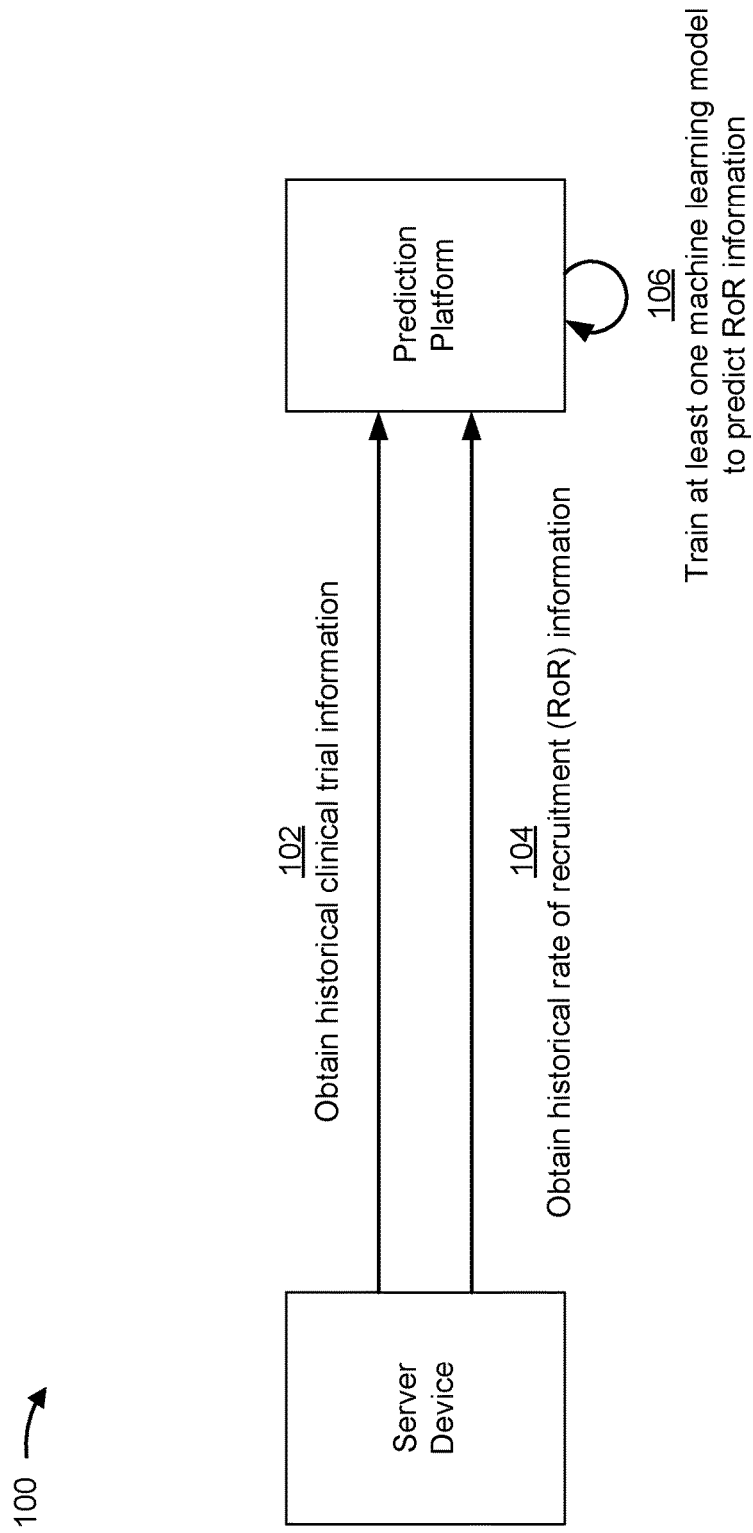
FIGS. 1A-1C are diagrams of example implementations described herein.

The following detailed description of example implementations refers to the accompanying drawings. The same reference numbers in different drawings may identify the same or similar elements.

Often, an organizer of a clinical trial (e.g., for a drug, for a therapy, for a treatment, and/or the like) determines how many participants are to participate in the clinical trial. Accordingly, in some cases, the organizer may need to determine an expected duration of the clinical trial (e.g., how many weeks, months, years, and/or the like the clinical trial is likely to last) and/or a number of clinical trial sites (also referred to as "sites") associated with the clinical trial (e.g., how many sites are to service the participants). In many cases, the organizer will use a metric, such as a rate of recruitment (RoR), to facilitate determining the duration of the clinical trial and/or the number of sites associated with the clinical trial. An RoR may indicate a rate of participants that can be recruited for the clinical trial per a period of time. For example, a linear RoR value may indicate an average number of participants that can be recruited per site, of multiple sites, associated with a clinical trial over a particular period of time, such as the duration of the clinical trial, a phase of the clinical trial, and/or the like, where all the sites are assumed to be actively recruiting participants during the particular period of time. As another example, a site-activated RoR value may indicate an average number of participants that can be recruited per site, of multiple sites, associated with a clinical trial over a particular period of time, where each site of the multiple sites may be actively recruiting participants during some or all of the particular period of time.

In many cases, the organizer has to estimate the RoR for a clinical trial while organizing the clinical trial (e.g., before the clinical trial is conducted). Because determining an accurate RoR estimate is difficult and reliant on many factors, in some cases the organizer incorrectly estimates a duration of the clinical trial and/or a number of sites associated with the clinical trial. This can lead to cost overruns or an inefficient uses of resources associated with planning the clinical trial.

Moreover, while the clinical trial is being conducted and due to an incorrect estimate of the duration of the clinical trial and/or the number of sites associated with the clinical trial, the organizer may use resources (e.g., processing resources, memory resources, power resources, communication resources, and/or the like) of one or more devices, such as a user device, a server device, a networking device, and/or the like to change aspects of the clinical trial to affect the duration of the clinical trial and/or the number of sites associated with the clinical trial while the clinical trial is being conducted.

Some implementations described herein provide a prediction platform that may determine (e.g., using at least one machine learning model) RoR information concerning a clinical trial. In some implementations, the prediction platform may obtain historical clinical trial information and historical RoR information and train a plurality of machine learning models based on the historical clinical trial information and the historical RoR information. In some implementations, the prediction platform may obtain identification information concerning a clinical trial, selection information concerning the clinical trial, and input information concerning the clinical trial. In some implementations, the prediction platform may select at least one machine learning model, of the plurality of machine learning models, based on the identification information and/or the selection information, and may process, using the at least one machine learning model, the input information to determine predicted RoR information concerning the clinical trial. In some implementations, the prediction platform may obtain present RoR information concerning the clinical trial (e.g., while the clinical trial is being conducted), may determine a status of the clinical trial based on the present RoR information and the predicted RoR information, and may cause, based on the determined status of the clinical trial, at least one action to be performed.

In this way, the prediction platform may provide a more accurate RoR estimate, which prevents cost overruns or an inefficient uses of resources associated with planning the clinical trial. Moreover, the prediction platform reduces a demand for resources (e.g., processing resources, memory resources, power resources, communication resources, and/or the like) that would otherwise be used by one or more devices to change aspects of the clinical trial to affect the duration of the clinical trial and/or the number of sites associated with the clinical trial while the clinical trial is being conducted. For example, the prediction platform may determine predicted RoR information that is more accurate than an organizer could estimate, which decreases a likelihood that the duration of the clinical trial and/or the number of sites associated with the clinical trial need to be changed. Moreover, the prediction platform may cause at least one action to be performed (e.g., providing alerts regarding performance of the clinical trial), which may reduce a need for the organizer to monitor the clinical trial using the one or more devices.

Figure 1B:
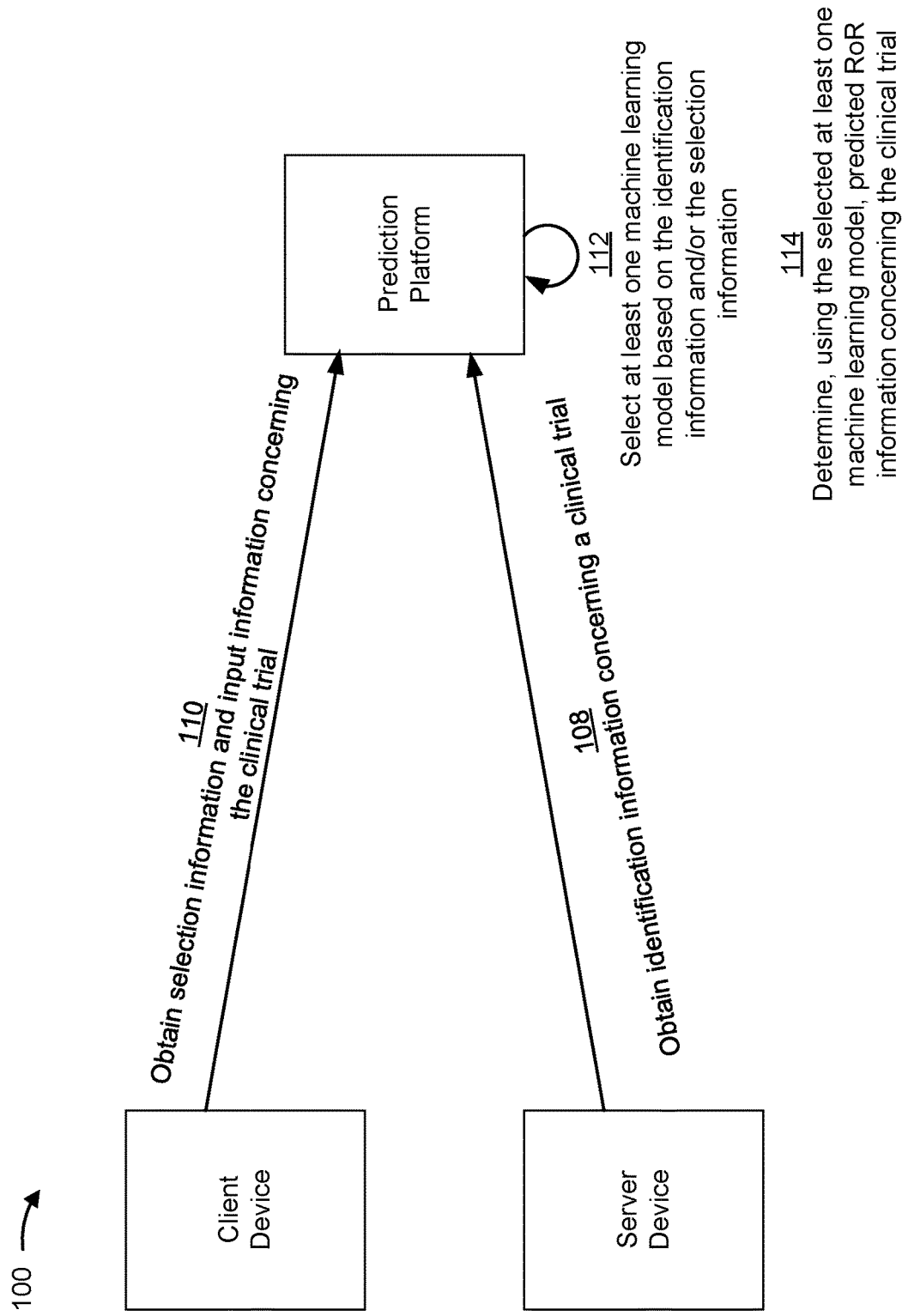
Figure 1C:
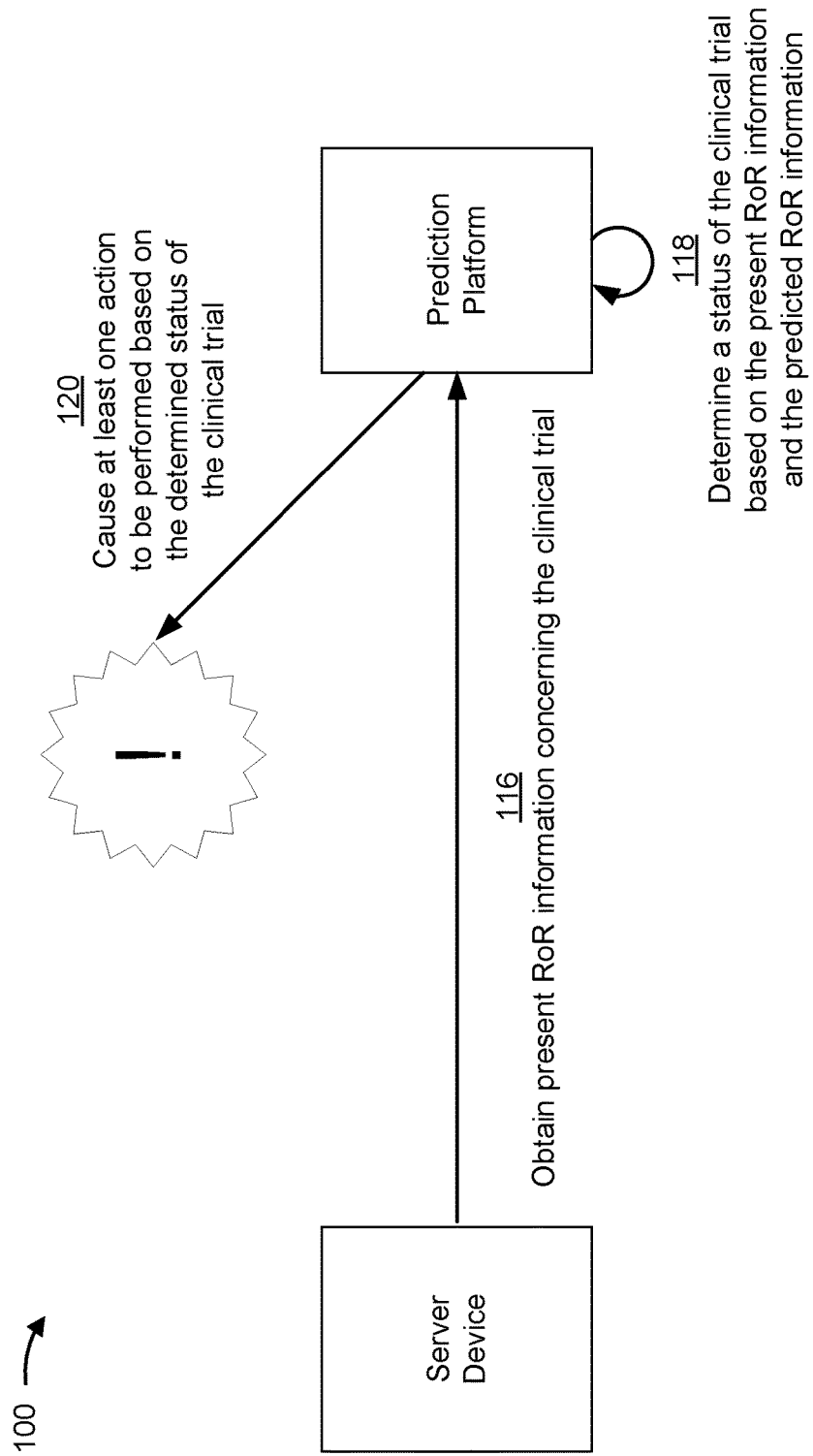

FIGS. 1A-1C are diagrams of example implementation(s) 100 described herein. As shown in FIGS. 1A-1C, example implementation(s) 100 may include a server device and/or a prediction platform. As shown in FIG. 1B, example implementation(s) 100 may also include a client device. In some implementations, the server device, the client device, and/or the prediction platform may be connected via a network, such as a wired network (e.g., the Internet or another data network), a wireless network (e.g., a wireless local area network, a wireless wide area network, a cellular network, etc.), and/or the like. Some example implementations described herein concern a single server device, a single client device, and/or a single prediction platform, but implementations can include a plurality of server devices, a plurality of client devices, and/or a plurality of prediction platforms.

As shown in FIG. 1A and by reference number 102, the prediction platform may obtain historical clinical trial information. For example, the server device may send the historical clinical trial information to the prediction platform and/or the prediction platform may request and receive the historical clinical trial information from the server device. The historical clinical trial information may include historical information concerning incidence and/or prevalence of a disease, historical information concerning real-world evidence of treating the disease, information concerning inclusion and exclusion criteria associated with one or more previous clinical trials concerning the disease, information concerning results of the one or more previous clinical trials concerning the disease, and/or the like. In some implementations, the historical clinical trial information may include information concerning market constraints associated with the disease and/or the one or more previous clinical trials, information concerning a competitive landscape associated with the disease and/or the one or more previous clinical trials, information concerning a drug landscape associated with the disease and/or the one or more previous clinical trials, information concerning a regulatory landscape associated with the disease and/or the one or more previous clinical trials, information concerning a performance and/or a capability of a clinical trial site (also referred to as a "site") associated with the disease and/or the one or more previous clinical trials, information concerning investigator enthusiasm regarding the disease and/or the one or more previous clinical trials, information concerning geographic areas associated with the disease and/or the one or more previous clinical trials, information concerning burdens on patients inflicted with the disease, information concerning burdens on the patient resulting from participation in the clinical trial, and/or the like. While some implementations described herein are directed to clinical trials associated with a disease, additional implementations also include clinical trials associated with therapies (e.g., physical therapies, psychological therapies, and/or the like), medical devices, drugs, drug treatment plans, and/or the like.

As shown by reference number 104, the prediction platform may obtain historical RoR information. For example, the server device may send the historical RoR information to the prediction platform and/or the prediction platform may request and receive the historical RoR information from the server device. The historical RoR information may include respective RoR values associated with the one or more previous clinical trials identified in the historical clinical trial information, respective durations of the one or more previous clinical trials, respective numbers of sites associated with the one or more previous clinical trials, and/or the like. In some implementations, the historical clinical trial information may include the historical RoR information.

As shown by reference number 106, the prediction platform may generate and/or train a machine learning model to predict RoR information. For example, the prediction platform may process the historical clinical trial information and/or the historical RoR information (hereinafter collectively referred to as the "historical information") to generate and/or train a machine learning model to predict RoR information. The predicted RoR information may include a predicted RoR value concerning a clinical trial, a predicted duration of the clinical trial, a predicted number of sites associated with the clinical trial, and/or the like.

In some implementations, the prediction platform may perform a set of data manipulation procedures to pre-process the historical information to generate the machine learning model. The prediction platform may use a data pre-processing procedure, a model training procedure, a model verification procedure, and/or the like to pre-process the historical information to generate processed historical information. For example, the prediction platform may pre-process the historical information to remove irrelevant information, confidential data, corrupt data, and/or the like; to replace personal information with generic information; to infer and/or to address missing information and/or to remove records that include missing information; and/or the like. In this way, the prediction platform may organize thousands, millions, or billions of data entries for machine learning and model generation.

In some implementations, the prediction platform may perform a training operation when generating the machine learning model. For example, the prediction platform may portion the historical information into a training set (e.g., a set of data to train the model), a validation set (e.g., a set of data used to evaluate a fit of the model and/or to fine tune the model), a test set (e.g., a set of data used to evaluate a final fit of the model), and/or the like. In some implementations, a minimum feature set may be created from pre-processing and/or dimensionality reduction of the historical information. In some implementations, the prediction platform may train the machine learning model on this minimum feature set, thereby reducing processing required to train the machine learning model, and may apply a classification technique to the minimum feature set.

When training the machine learning model, the prediction platform may utilize a random forest classifier technique to train the machine learning model. For example, the prediction platform may utilize a random forest classifier technique to construct multiple decision trees during training and may output a classification of the historical information. As another example, the prediction platform may utilize a random forest regression technique to construct multiple decision trees during training and may output a numeric predication associated with the historical information. Additionally, or alternatively, when training the machine learning model, the prediction platform may utilize one or more gradient boosting techniques to generate the machine learning model. For example, the prediction platform may utilize an xgboost classifier technique, an xgboost regression technique, a gradient boosting machine (GBM) technique, a gradient boosting tree, and/or the like to generate a prediction model from a set of weak prediction models.

When training the machine learning model, the prediction platform may utilize a logistic regression technique to train the machine learning model. For example, the behavioral analytics platform may utilize a binary classification of the historical information (e.g., whether the historical information is indicative of a particular accurate prediction), a multi-class classification of the historical information (e.g., whether the historical information is indicative of one or more accurate predictions), and/or the like to train the machine learning model. Additionally, or alternatively, when training the machine learning model, the prediction platform may utilize a naïve Bayes classifier technique to train the machine learning model. For example, the behavioral analytics platform may utilize binary recursive partitioning to divide the historical information into various binary categories (e.g., starting with whether the historical information is indicative of a particular accurate prediction). Based on using recursive partitioning, the prediction platform may reduce utilization of computing resources relative to manual, linear sorting and analysis of data points, thereby enabling use of thousands, millions, or billions of data points to train a machine learning model, which may result in a more accurate machine learning model than using fewer data points.

Additionally, or alternatively, when training the machine learning model, the prediction platform may utilize a support vector machine (SVM) classifier technique. For example, the prediction platform may utilize a linear model to implement non-linear class boundaries, such as via a max margin hyperplane. Additionally, or alternatively, when utilizing the SVM classifier technique, the prediction platform may utilize a binary classifier to perform a multi-class classification. Use of an SVM classifier technique may reduce or eliminate overfitting, may increase a robustness of the machine learning model to noise, and/or the like.

In some implementations, the prediction platform may train the machine learning model using a supervised training procedure. In some implementations, the prediction platform may receive additional input to the machine learning model from a subject matter expert. In some implementations, the prediction platform may use one or more other model training techniques, such as a neural network technique, a latent semantic indexing technique, and/or the like. For example, the prediction platform may perform a multi-layer artificial neural network processing technique (e.g., using a recurrent neural network architecture, a two-layer feedforward neural network architecture, a three-layer feedforward neural network architecture, and/or the like) to perform pattern recognition with regard to patterns in the historical information. In this case, use of the artificial neural network processing technique may improve an accuracy of a supervised learning model generated by the prediction platform by being more robust to noisy, imprecise, or incomplete data, and by enabling the prediction platform to detect patterns and/or trends undetectable to human analysts or systems using less complex techniques. Furthermore, when using a recurrent neural network architecture, long short-term memory (LSTM) may be employed to classify, make predictions, and/or otherwise process time-series data, which may be useful to predict how patterns change over time (e.g., over a month, a year, and/or the like).

Additionally, or alternatively, when training the machine learning model, the prediction platform may utilize a feature engineering technique to divide the historical information into various binary classifications (e.g., classifications based on percentiles, such as a $0^{th}$ to $19^{th}$ percentile classification, a $20^{th}$ to $39^{th}$ percentile classification, a $40^{th}$ to $59^{th}$ percentile classification, a $60^{th}$ to $79^{th}$ percentile classification, a $80^{th}$ to $99^{th}$ percentile classification, and/or the like). The prediction platform may perform natural language processing (e.g., using a bag of words processing technique, comparing a Jaccard distance between the binary classifications and/or different sets of words, and/or the like) to identify parameters, such as key words, n-grams, phrases, relationships, concepts, and/or the like associated with the historical information and/or the binary classifications and to select featured parameters that are related to patterns or trends of the historical information.

In some implementations, a different device, such as the server device, may generate and train the machine learning model. The prediction platform may obtain the machine learning model from the different device. For example, the different device may send the machine learning model to the prediction platform and/or the prediction platform may request and receive the machine learning model from the different device. In some implementations, the different device may update and send (e.g., on a scheduled basis, on an on-demand basis, on a triggered basis, and/or the like) the machine learning model to the prediction platform. The prediction platform may obtain the updated machine learning model from the different device.

Additionally, or alternatively, instead of generating and/or training just one machine learning model, the prediction platform may generate and/or train one or more machine learning models in a similar manner. For example, the prediction platform may determine that a first machine learning model that uses a first particular machine learning model technique provides a better fit for determining predicted RoR information for first particular historical information. Further, the prediction platform may determine that a second machine learning model that uses a second particular machine learning model technique provides a better fit for determining predicted RoR information for second particular historical information, and/or the like. Accordingly, the prediction platform may separately generate and/or train the first particular machine learning model and may separately generate and/or train the second particular machine learning model. In this way, the prediction platform may use artificial intelligence techniques, machine learning techniques, deep learning techniques, and/or the like to determine one or more associations between historical information and predicted RoR information.

As shown in FIG. 1B and by reference number 108, the prediction platform may obtain identification information concerning a clinical trial (e.g., a clinical trial that has yet to be conducted). For example, the server device may send the identification information to the prediction platform and/or the prediction platform may request and receive the identification information from the server device. The identification information may include an identifier associated with a protocol that concerns the clinical trial (e.g., a unique identifier, such as a protocol identification number, a National Clinical Trial identifier, a European Clinical Trial identifier, a TrialTrove identifier, and/or the like), a version associated with the protocol, a phase associated with the protocol, a title associated with the protocol, and/or the like.

As shown by reference number 110, the prediction platform may obtain selection information concerning the clinical trial (e.g., information the processing platform may process to select at least one machine learning model to determine predicted RoR information concerning the clinical trial) and/or input information concerning the clinical trial (e.g., information the processing platform may process using the selected at least one machine learning model to determine the predicted RoR information concerning the clinical trial). For example, the client device may send the selection information and/or the input information to the prediction platform and/or the prediction platform may request and receive the selection information and/or the input information from the client device. The selection information may include a total number of participants participating in the clinical trial, a total number of sites associated with the clinical trial, information identifying one or more geographic areas associated with the clinical trial, information identifying and/or associated with one or more sites associated with the clinical trial, information concerning approval of a protocol associated with the clinical trial, information concerning activation of a first site associated with the clinical trial, information concerning a rarity of a disease, information concerning a sponsor of the clinical trial, information concerning a therapeutic area associated with the clinical trial, information concerning an indication associated with the clinical trial, and/or the like.

The input information may include information concerning an objective associated with the clinical trial, information concerning inclusion and exclusion criteria associated with the clinical trial, information concerning a primary end point (e.g., survivability, tolerability) associated with the clinical trial, information concerning an explicitly requested disease sub-type associated with the clinical trial, information concerning a specific disease characteristic associated with the clinical trial, information concerning a participant characteristic (e.g., a participant age span, whether the participant has had first line treatment, whether the participant has had second line treatment, whether the participant has a particular genetic mutation, and/or the like) associated with the clinical trial, information concerning a targeted indication associated with the clinical trial, information concerning geographic areas associated with the clinical trial (e.g., a country, a site within a country, and/or the like associated with the clinical trial), information concerning an initiator (e.g., an investigator) associated with the clinical trial, information identifying a sponsor (e.g., an academic institution, the National Institutes of Health (NIH), National Cancer Institute (NCI), and/or the like) associated with the clinical trial, information concerning a procedure (e.g., a biopsy) associated with the clinical trial, and/or the like. In some implementations, the input information may include, information concerning a therapeutic area associated with the clinical trial, information concerning an indication associated with the clinical trial, information concerning targeted participant population information associated with the clinical trial, information concerning treatment arms associated with the clinical trial, information concerning design of a protocol associated with the clinical trial, and/or the like.

In some implementations, the prediction platform may provide a user interface for a user (e.g., a user of the client device) to input information to the prediction platform that causes the prediction platform to obtain the identification information, the selection information, and/or the input information. For example, the user may enter, using the client device and via the user interface, an identifier associated with a protocol and the prediction platform may communicate, based on the identifier, with the server device to obtain the identification information. In this case, the server device may be associated with a clinical trial management system (CTMS) and/or the like. As another example, the user may enter, using the client device and via the user interface, an identifier associated with the protocol and the prediction platform may communicate, based on the identifier, with the client device and/or the server device to automatically obtain the selection information and/or the input information. Additionally, or alternatively, the prediction platform may obtain the selection information and/or the input information based on the identification information. For example, the prediction platform may, based on the identification information, provide a user interface tailored to obtain the selection information and/or the input information from the user via the client device. The user may enter, using the client device and via the user interface, the selection information and/or the input information.

In some implementations, the user interface may provide fields, checkboxes, sliders, and/or the like for entering the selection information and/or the input information by the user via the client device. The user interface may provide different fields, checkboxes, sliders, and/or the like based on the identification information. For example, the user interface may provide a different set of fields, checkboxes, sliders, and/or the like for each selection information element, each input information element, and/or the like. In a particular example, the user interface may provide a different set of fields, checkboxes, sliders, and/or the like based on the selection information and/or input information specifying an indication of lymphoma, hematology and oncology, inflammation and immunology, solid tumor, myeloid, and/or the like.

As shown by reference number 112, the prediction platform may select at least one machine learning model to determine predicted RoR information concerning the clinical trial. The prediction platform may select at least one machine learning model from the one or more machine learning models generated and/or trained by the prediction platform. The prediction platform may select the at least one machine learning model based on the identification information and/or the selection information. For example, the prediction platform may identify the one or more machine learning models, may determine that the identification information and/or selection information comprises one or more elements (e.g., an identifier associated with a protocol that concerns the clinical trial, a total number of participants participating in the clinical trial, a total number of sites associated with the clinical trial, information identifying geographic areas associated with the clinical trial, and/or the like), may process the one or more elements to identify at least one particular element of the one or more elements (e.g., that has a relationship of high predictive significance with at least one particular machine learning model), and may select the at least one machine learning model based on the at least one particular element.

In a particular example, the prediction platform may select at least one machine learning model that uses a naïve Bayes classifier machine learning model technique for first particular identification information and/or first particular selection information. In an additional example, the prediction platform may select at least one machine learning model that uses a gradient boosting machine learning model technique for second particular identification information and/or second particular selection information. In this way, the prediction platform may select, based on the identification information and/or the selection information, the best set of machine learning models (e.g., an ensemble model of machine learning models), of a plurality of machine learning models generated and/or trained by the prediction platform, to determine predicted RoR information.

In some implementations, the prediction platform may process, using at least one additional machine learning model, the identification information and the selection information to select the at least one machine learning model. In some implementations, the prediction platform may request and receive, generate, and/or train the at least one additional machine learning model in a similar manner as described herein in relation to the at least one machine learning model. For example, the prediction platform may obtain historical identification information and/or historical selection information (hereinafter collectively referred to as the "additional historical information") to generate and/or train the at least one additional machine learning model. In some implementations, the prediction platform may process the additional historical information to train the at least one additional machine learning model to select, for particular identification information and/or particular selection information, a particular at least one machine learning model of the one or more machine learning models. In some implementations, the prediction platform may perform a set of data manipulation procedures, perform a training operation, use a classification technique, perform a recursive feature elimination procedure, and/or the like, as described herein, to determine an association between identification information and/or selection information and at least one machine learning model.

As shown by reference number 114, the prediction platform may determine predicted RoR information concerning the clinical trial using the selected at least one machine learning model. The predicted RoR information may include a predicted RoR value concerning the clinical trial, a predicted duration of the clinical trial, a predicted number of sites associated with the clinical trial, and/or the like. Additionally, or alternatively, the predicted RoR information may include a plurality of predicted RoR values concerning the clinical trial; a plurality of predicted durations concerning the clinical trial, wherein each predicted duration, of the plurality of predicted durations, is associated with a respective predicted RoR value of the plurality of predicted RoR values; and a plurality of predicted numbers of sites associated with the clinical trial, wherein each predicted number of sites, of the plurality of predicted numbers of sites, is associated with a respective predicted RoR value of the plurality of predicted RoR values. Each of the predicted RoR values may be associated with a geographic area (e.g., each predicted RoR value may be respectively associated with a geographic area of one or more geographic areas identified in the selection and/or input information).

In some implementations, the prediction platform may process, using the selected at least one machine learning model, the input information to determine the predicted RoR. For example, the selected at least one machine learning model may use a naïve Bayes classifier machine learning model technique, a gradient boosting regressor machine learning model technique, and/or the like to process the input information to determine the predicted RoR. In some implementations, the prediction platform may process the input information to identify parameters, such as key words, n-grams, phrases, relationships, concepts, and/or the like associated with the clinical trial and may process the parameters using the selected at least one machine learning model to determine the predicted RoR information.

In some implementations, the prediction platform may cause the predicted RoR information to be displayed on a display of another device, such as the client device. For example, the prediction platform may provide a user interface that enables the predicted RoR information to be displayed on a display of the client device.

As shown in FIG. 1C and by reference number 116, the prediction platform may obtain present RoR information concerning the clinical trial (e.g., RoR information concerning the clinical trial when the clinical trial is conducted). For example, while the clinical trial is being conducted, the server device may send the present RoR information to the prediction platform and/or the prediction platform may request and receive the present RoR information from the server device. The present RoR information may include a present RoR value concerning the clinical trial, a present duration of the clinical trial, a present number of sites associated with the clinical trial, a present number of recruited and/or enrolled individuals, and/or the like. Additionally, or alternatively, the present RoR information may include a plurality of present RoR values concerning the clinical trial; a plurality of present durations concerning the clinical trial, wherein each present duration, of the plurality of present durations, is associated with a respective present RoR value of the plurality of present RoR values; a plurality of present numbers of sites associated with the clinical trial, wherein each present number of sites, of the plurality of present numbers of sites, is associated with a respective present RoR value of the plurality of present RoR values; and a plurality of present numbers of recruited and/or enrolled individuals, wherein each present number of recruited and/or enrolled individuals, of the plurality of present numbers or recruited and/or enrolled individuals, is associated with a respective preset RoR value of the plurality of present RoR values. Each of the present RoR values may be associated with a geographic area (e.g., each present RoR value may be respectively associated with a geographic area of one or more geographic areas identified in the input information), with a specific disease characteristic (e.g., each present RoR value may be associated with a specific disease characteristic identified in the input information), with a participant characteristic (e.g., each present RoR value may be associated with a participant characteristic identified in the input information), and/or the like.

As shown by reference number 118, the prediction platform may determine a status of the clinical trial (e.g., while the clinical trial is being conducted). The prediction platform may determine the status based on the present RoR information and the predicted RoR information. For example, the prediction platform may determine, based on the present RoR information, a present RoR value concerning the clinical trial and may determine, based on the predicted RoR information, a predicted RoR value concerning the clinical trial. The prediction platform may determine a difference between the present RoR value and the predicted RoR value and may determine the status based on the difference. In another example, the prediction platform may determine, based on the present RoR information, an estimated duration of the clinical trial and may determine, based on the predicted RoR information, a predicted duration of the clinical trial. The prediction platform may determine a difference between the estimated duration and the predicted duration and may determine the status based on the difference. As another example, the prediction platform may determine, based on the present RoR information, one or more present RoR values (e.g., where each present RoR value is associated with a geographic area) and may determine, based on the predicted RoR information, one or more predicted RoR values (e.g., where each predicted RoR value is associated with a geographic area). The prediction platform may determine, for a geographic area of one or more geographic areas, a difference between an associated present RoR value and an associated predicted RoR value, and may determine the status based on the respective difference associated with each geographic area of the one or more geographic areas. The determined status may indicate that the clinical trial is performing as expected (e.g., the present RoR value equals the predicted RoR value, within a threshold amount, such as 3%, 5%, 10%, and/or the like, of the predicted RoR value), that the clinical trial is underperforming (e.g., the present RoR value is less than a function of the predicted RoR value (e.g. the predicted RoR value minus the threshold amount)), that the clinical trial is overperforming (e.g., the present RoR value is greater than a function of the predicted RoR value (e.g., the predicted RoR value plus the threshold amount)), and/or the like.

As shown by reference number 120, the prediction platform may cause an action to be performed based on the determined status of the clinical trial. For example, the prediction platform may cause the selected at least one machine learning model to be updated based on the present RoR information, the predicted RoR information, the determined status, the input information, the selection information, the identification information, and/or the like. In some implementations, the prediction platform may cause the selected at least one machine learning model to be updated when the determined status indicates that the clinical trial is underperforming or overperforming. As another example, the prediction platform may process the present RoR information, the predicted RoR information, the determined status, the input information, and/or the like using the selected at least one machine learning model (e.g., after the at least one machine learning model has been updated) to cause the predicted RoR value concerning the clinical trial to be updated.

As another example, the prediction platform may generate an alert concerning the determined status of the clinical trial and may cause a different device, such as the client device, to display the alert on a display of the different device. The alert (e.g., an electronic mail message, a text message, a popup message, a notification, and/or the like) may include information indicating the determined status of the clinical trial. In another example, the prediction platform may generate, based on the determined status, a message indicating that a duration of the clinical trial and/or a number of sites associated with the clinical trial is to be changed and may cause a different device, such as the client device, to display the message on a display of the different device. The message may recommend that the duration of the clinical trial should be extended and/or the number of sites should be increased when the determined status indicates that the clinical trial is underperforming. Additionally, or alternatively, the message may recommend that the duration of the clinical trial should be reduced and/or the number of sites should be decreased when the determined status indicates that the clinical trial is overperforming.

As indicated above, FIGS. 1A-1C are provided merely as an example. Other examples may differ from what is described with regard to FIGS. 1A-1C.

Figure 2:
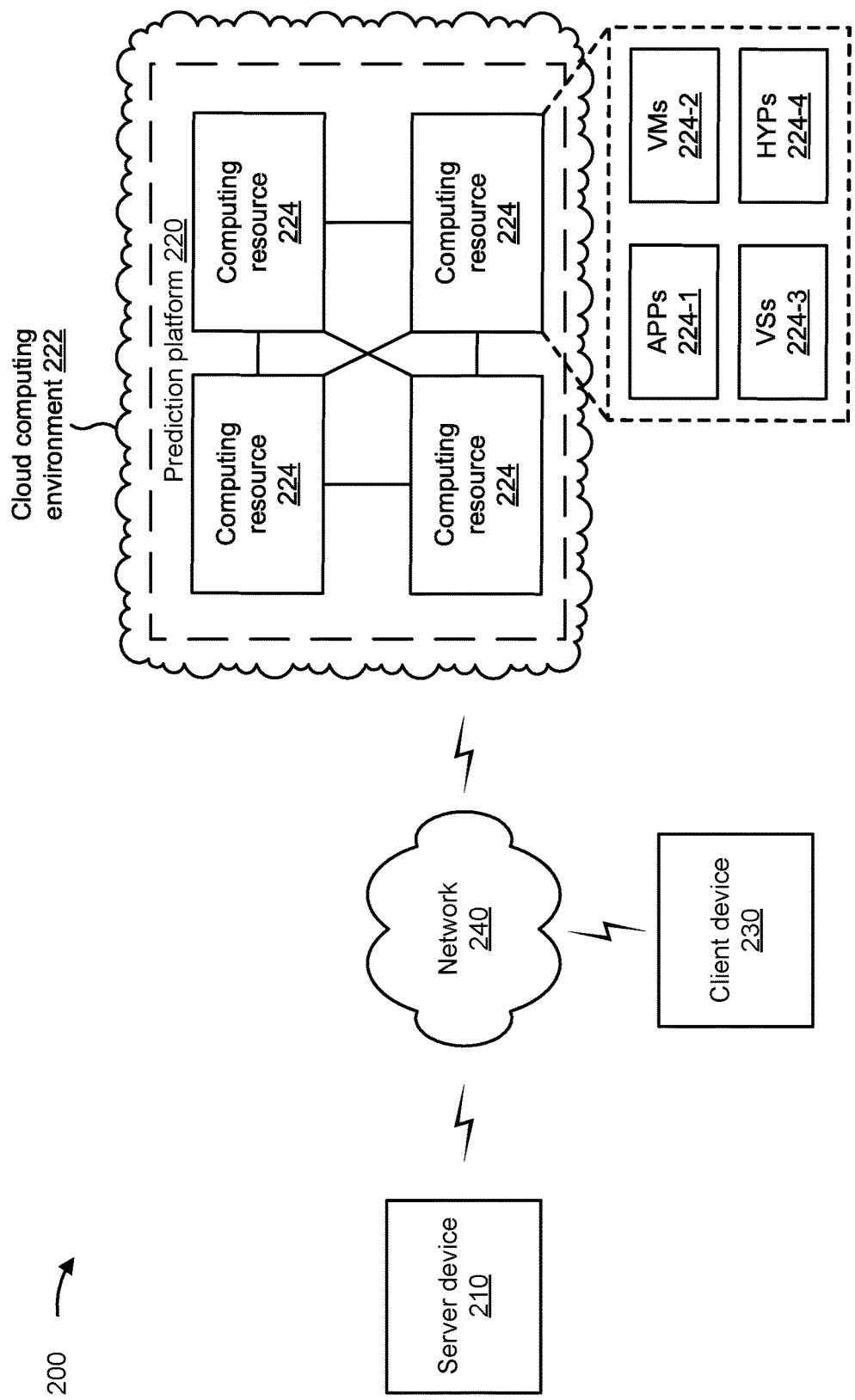
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a server device 210, a prediction platform 220 in a cloud computing environment 222 that includes computing resources 224, a client device 230, a network 240, and/or the like. Devices of environment 200 may interconnect via wired connections, wireless connections, or a combination of wired and wireless connections.

Server device 210 includes one or more devices capable of receiving, generating, storing, processing, and/or providing information, such as information described herein. For example, server device 210 may include a laptop computer, a tablet computer, a desktop computer, a server, a group of servers, or a similar type of device. In some implementations, server device 210 may receive information from and/or transmit information to prediction platform 220, client device 230, and/or the like.

Prediction platform 220 includes one or more devices that may determine rate of recruitment (RoR) information concerning a clinical trial. In some implementations, prediction platform 220 may be modular such that certain software components may be swapped in or out depending on a particular need. As such, prediction platform 220 may be easily and/or quickly reconfigured for different uses. In some implementations, prediction platform 220 may receive information from and/or transmit information server device 210, client device 230, and/or the like.

In some implementations, as shown, prediction platform 220 may be hosted in a cloud computing environment 222. Notably, while implementations described herein describe prediction platform 220 as being hosted in cloud computing environment 222, in some implementations, prediction platform 220 may be non-cloud-based (i.e., may be implemented outside of a cloud computing environment) or may be partially cloud-based.

Cloud computing environment 222 includes an environment that may host prediction platform 220. Cloud computing environment 222 may provide computation, software, data access, storage, etc. services that do not require end-user knowledge of a physical location and configuration of system(s) and/or device(s) that host prediction platform 220. As shown, cloud computing environment 222 may include a group of computing resources 224 (referred to collectively as "computing resources 224" and individually as "computing resource 224").

Computing resource 224 includes one or more personal computers, workstation computers, server devices, or other types of computation and/or communication devices. In some implementations, computing resource 224 may host prediction platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by client device 230. Application 224-1 may eliminate a need to install and execute the software applications on client device 230. For example, application 224-1 may include software associated with prediction platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system ("OS"). A process virtual machine may execute a single program and may support a single process. In some implementations, virtual machine 224-2 may execute on behalf of a user (e.g., a user of server device 210 and/or client device 230 or an operator of prediction platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may provide administrators of the storage system with flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems and may manage the execution of the guest operating systems. Multiple instances of a variety of operating systems may share virtualized hardware resources.

Client device 230 includes one or more devices capable of receiving, generating, storing, processing, and/or providing information, such as information described herein. For example, client device 230 may include a computer (e.g., a desktop computer, a laptop computer, a tablet computer, a handheld computer, a server device, etc.), a mobile phone (e.g., a smart phone, a radiotelephone, etc.), an internet of things (IoT) device or smart appliance, or a similar device. In some implementations, client device 230 may receive information from and/or transmit information to server device 210, prediction platform 220, and/or the like.

Network 240 includes one or more wired and/or wireless networks. For example, network 240 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device and/or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
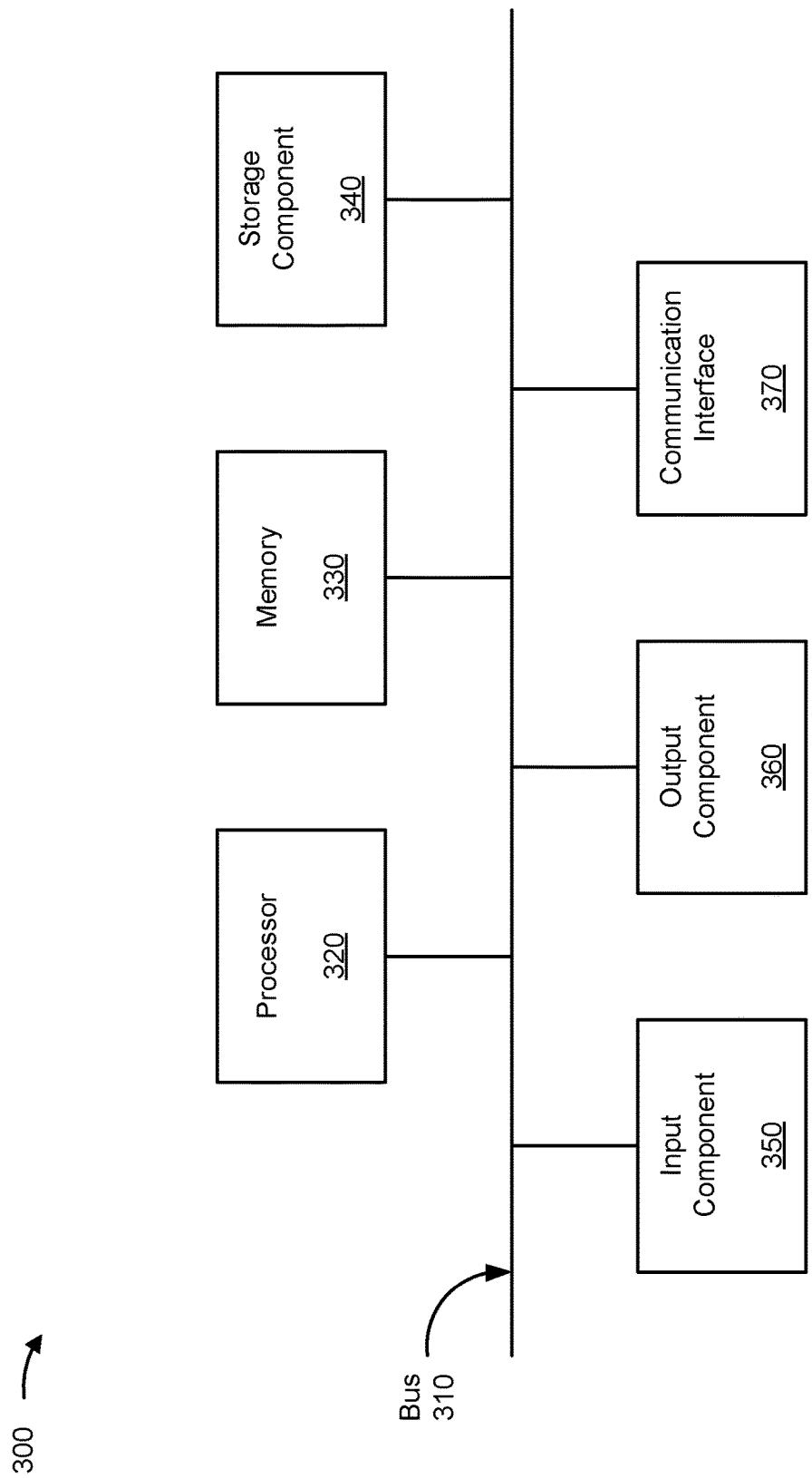
FIG. 3 is a diagram of example components of one or more devices of FIG. 2.

FIG. 3 is a diagram of example components of a device 300. Device 300 may correspond to server device 210, prediction platform 220, computing resource 224, and/or client device 230. In some implementations, server device 210, prediction platform 220, computing resource 224, and/or client device 230 may include one or more devices 300 and/or one or more components of device 300. As shown in FIG. 3, device 300 may include a bus 310, a processor 320, a memory 330, a storage component 340, an input component 350, an output component 360, and/or a communication interface 370.

Bus 310 includes a component that permits communication among multiple components of device 300. Processor 320 is implemented in hardware, firmware, and/or a combination of hardware and software. Processor 320 takes the form of a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a component for determining location (e.g., a global positioning system (GPS) component) and/or a sensor (e.g., an accelerometer, a gyroscope, an actuator, another type of positional or environmental sensor, and/or the like). Output component 360 includes a component that provides output information from device 300 (via, e.g., a display, a speaker, a haptic feedback component, an audio or visual indicator, and/or the like).

Communication interface 370 includes a transceiver-like component (e.g., a transceiver, a separate receiver, a separate transmitter, and/or the like) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. As used herein, the term "computer-readable medium" refers to a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
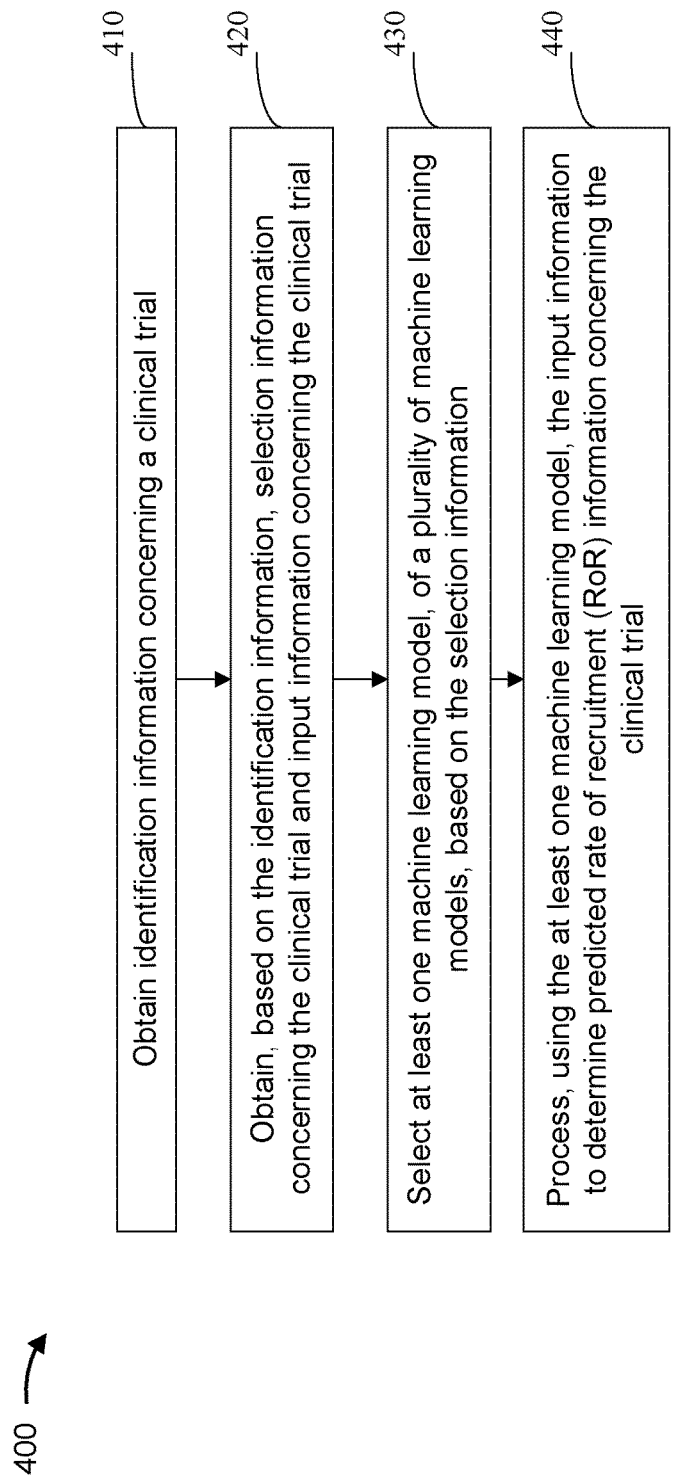
FIGS. 4-6 are flow charts of example processes for determining rate of recruitment (RoR) information concerning a clinical trial.

FIG. 4 is a flow chart of an example process 400 for determining rate of recruitment (RoR) information concerning a clinical trial. In some implementations, one or more process blocks of FIG. 4 may be performed by a prediction platform (e.g., prediction platform 220). In some implementations, one or more process blocks of FIG. 4 may be performed by another device or a group of devices separate from or including the prediction platform, such as a server device (e.g., server device 210), a client device (e.g., client device 230), and/or the like.

As shown in FIG. 4, process 400 may include obtaining identification information concerning a clinical trial (block 410). For example, the prediction platform (e.g., using computing resource 224, processor 320, memory 330, storage component 340, input component 350, output component 360, communication interface 370, and/or the like) may obtain identification information concerning a clinical trial, as described above.

As further shown in FIG. 4, process 400 may include obtaining, based on the identification information, selection information concerning the clinical trial and input information concerning the clinical trial (block 420). For example, the prediction platform (e.g., using computing resource 224, processor 320, memory 330, storage component 340, input component 350, output component 360, communication interface 370, and/or the like) may obtain, based on the identification information, selection information concerning the clinical trial and input information concerning the clinical trial, as described above.

As further shown in FIG. 4, process 400 may include selecting at least one machine learning model, of a plurality of machine learning models, based on the selection information (block 430). For example, the prediction platform (e.g., using computing resource 224, processor 320, memory 330, storage component 340, input component 350, output component 360, communication interface 370, and/or the like) may select at least one machine learning model, of a plurality of machine learning models, based on the selection information, as described above.

As further shown in FIG. 4, process 400 may include processing, using the at least one machine learning model, the input information to determine predicted rate of recruitment (RoR) information concerning the clinical trial (block 440). For example, the prediction platform (e.g., using computing resource 224, processor 320, memory 330, storage component 340, input component 350, output component 360, communication interface 370, and/or the like) may process, using the at least one machine learning model, the input information to determine predicted rate of recruitment (RoR) information concerning the clinical trial, as described above.

Process 400 may include additional implementations, such as any single implementation or any combination of implementations described below and/or in connection with one or more other processes described elsewhere herein.

In a first implementation, the prediction platform may obtain present RoR information concerning the clinical trial, may determine a status of the clinical trial based on the present RoR information and the predicted RoR information, and may cause, based on the determined status of the clinical trial, at least one action to be performed.

In a second implementation, when causing the at least one action to be performed, the prediction platform may cause the at least one machine learning model to be updated based on at least one of the present RoR information, the predicted RoR information, the determined status, the input information, the selection information, or the identification information; or the prediction platform may process, using the at least one machine learning model, the present RoR information, the predicted RoR information, the determined status, or the input information to cause a predicted RoR value concerning the clinical trial of the RoR information to be updated.

In a third implementation, alone or in combination with the first implementation, the identification information may include at least one of: an identifier associated with a protocol that concerns the clinical trial; a version associated with the protocol; a phase associated with the protocol; a title associated with the protocol; a franchise associated with the protocol; a therapeutic area associated with the protocol; an indication associated with the protocol; targeted participant population information associated with the protocol; treatment arms information associated with the protocol; or protocol design information associated with the protocol.

In a fourth implementation, alone or in combination with one or more of the first through third implementations, the selection information may include at least one of: a total number of participants participating in the clinical trial; a total number of sites associated with the clinical trial; information identifying geographic areas associated with the clinical trial; information identifying and/or associated with one or more sites associated with the clinical trial; information concerning approval of a protocol associated with the clinical trial; information concerning activation of a first site associated with the clinical trial; information concerning a rarity of a disease; information concerning a sponsor of the clinical trial; information concerning a therapeutic area associated with the clinical trial; or information concerning an indication associated with the clinical trial.

In a fifth implementation, alone or in combination with one or more of the first through fourth implementations, the input information may include at least one of: information concerning an objective associated with the clinical trial; information concerning a primary end point associated with the clinical trial; information concerning an explicitly requested disease sub-type associated with the clinical trial; information concerning a specific disease characteristic associated with the clinical trial; information concerning a participant characteristic associated with the clinical trial; information concerning a targeted indication associated with the clinical trial; information concerning geographic areas associated with the clinical trial; information concerning an initiator associated with the clinical trial; information identifying a sponsor associated with the clinical trial; or information concerning a procedure associated with the clinical trial.

In a sixth implementation, alone or in combination with one or more of the first through fifth implementations, the predicted RoR information may include at least one of: a predicted RoR value concerning the clinical trial; a predicted duration of the clinical trial; or a predicted number of sites associated with the clinical trial.

In a seventh implementation, alone or in combination with one or more of the first through sixth implementations, when selecting the at least one machine learning model, the prediction platform may identify the plurality of machine learning models; may determine that the selection information comprises one or more elements; may process the one or more elements to identify at least one particular element of the one or more elements; and may select the at least one machine learning model based on the at least one particular element.

In an eighth implementation, alone or in combination with one or more of the first through seventh implementations, when processing the input information to determine the predicted RoR information, the prediction platform may process the input information to identify parameters that include key words, phrases, relationships, or concepts associated with the clinical trial; and may process the parameters using the at least one machine learning model to determine the predicted RoR information.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
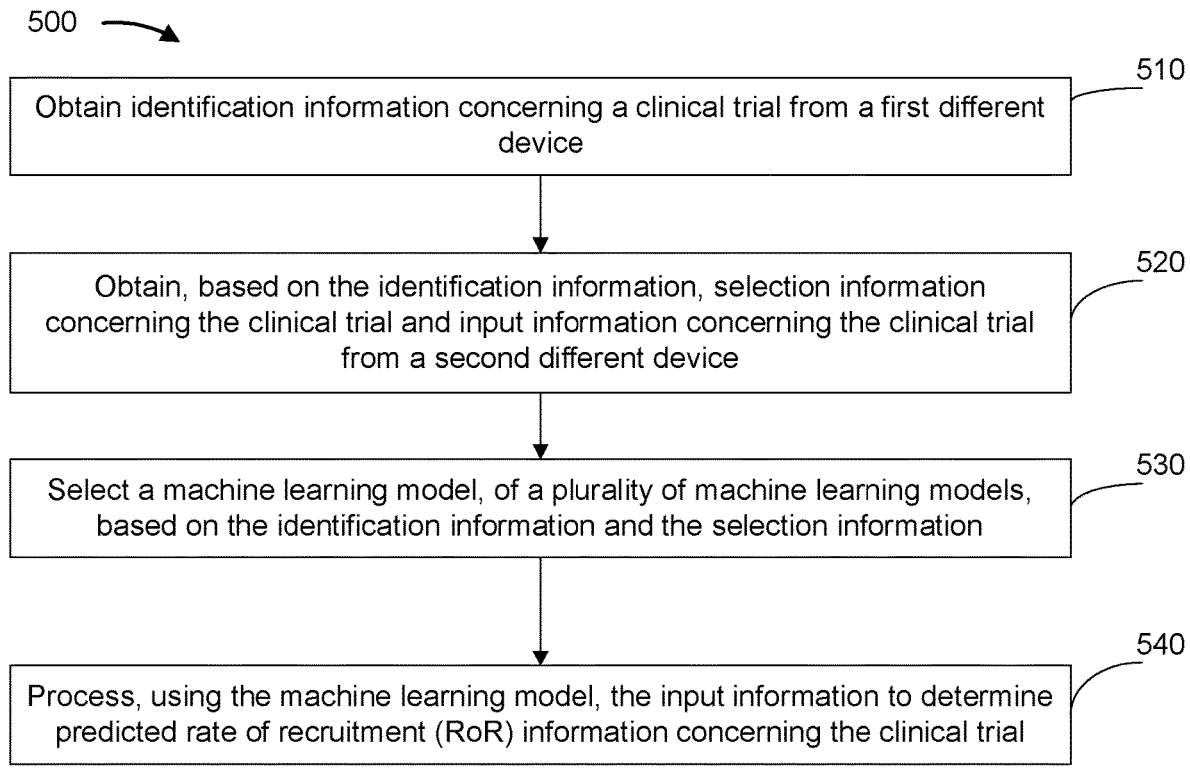

FIG. 5 is a flow chart of an example process 500 for determining rate of recruitment (RoR) information concerning a clinical trial. In some implementations, one or more process blocks of FIG. 5 may be performed by a prediction platform (e.g., prediction platform 220). In some implementations, one or more process blocks of FIG. 5 may be performed by another device or a group of devices separate from or including the prediction platform, such as a server device (e.g., server device 210), a client device (e.g., client device 230), and/or the like.

As shown in FIG. 5, process 500 may include obtaining identification information concerning a clinical trial from a first different device (block 510). For example, the prediction platform (e.g., using computing resource 224, processor 320, memory 330, storage component 340, input component 350, output component 360, communication interface 370, and/or the like) may obtain identification information concerning a clinical trial from a first different device, as described above.

As further shown in FIG. 5, process 500 may include obtaining, based on the identification information, selection information concerning the clinical trial and input information concerning the clinical trial from a second different device (block 520). For example, the prediction platform (e.g., using computing resource 224, processor 320, memory 330, storage component 340, input component 350, output component 360, communication interface 370, and/or the like) may obtain, based on the identification information, selection information concerning the clinical trial and input information concerning the clinical trial from a second different device, as described above.

As further shown in FIG. 5, process 500 may include selecting at least one machine learning model, of a plurality of machine learning models, based on the identification information and the selection information (block 530). For example, the prediction platform (e.g., using computing resource 224, processor 320, memory 330, storage component 340, input component 350, output component 360, communication interface 370, and/or the like) may select at least one machine learning model, of a plurality of machine learning models, based on the identification information and the selection information, as described above.

As further shown in FIG. 5, process 500 may include processing, using the at least one machine learning model, the input information to determine predicted rate of recruitment (RoR) information concerning the clinical trial (block 540). For example, the prediction platform (e.g., using computing resource 224, processor 320, memory 330, storage component 340, input component 350, output component 360, communication interface 370, and/or the like) may process, using the at least one machine learning model, the input information to determine predicted rate of recruitment (RoR) information concerning the clinical trial, as described above.

Process 500 may include additional implementations, such as any single implementation or any combination of implementations described below and/or in connection with one or more other processes described elsewhere herein.

In a first implementation, when selecting the at least one machine learning model, the prediction platform may process, using an at least one additional machine learning model, the identification information and the selection information to select the at least one machine learning model In a second implementation, alone or in combination with the first implementation, the prediction platform may obtain present RoR information concerning the clinical trial from the first different device; may determine a status of the clinical trial based on the present RoR information and the predicted RoR information; and may cause, based on the determined status of the clinical trial, at least one action to be performed. The present RoR information may include one or more present RoR values that are each respectively associated with one or more criteria included in the selection information.

In a third implementation, alone or in combination with one or more of the first and second implementations, when determining the status of the clinical trial, the prediction platform may determine, based on the present RoR information, the one or more present RoR values; may determine, based on the predicted RoR information, the one or more predicted RoR values; may determine, for each geographic area of one or more geographic areas, a difference between a present RoR value, of the one or more present RoR values, associated with the geographic area and a predicted RoR value, of the one or more predicted RoR values, associated with the geographic area; and may determine the status based on the respective difference associated with each geographic area of the one or more geographic areas.

In a fourth implementation, alone or in combination with one or more of the first through third implementations, when causing the at least one action to be performed, the prediction platform may generate an alert concerning the determined status of the clinical trial; and may cause a third different device to display the alert on a display of the third different device.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
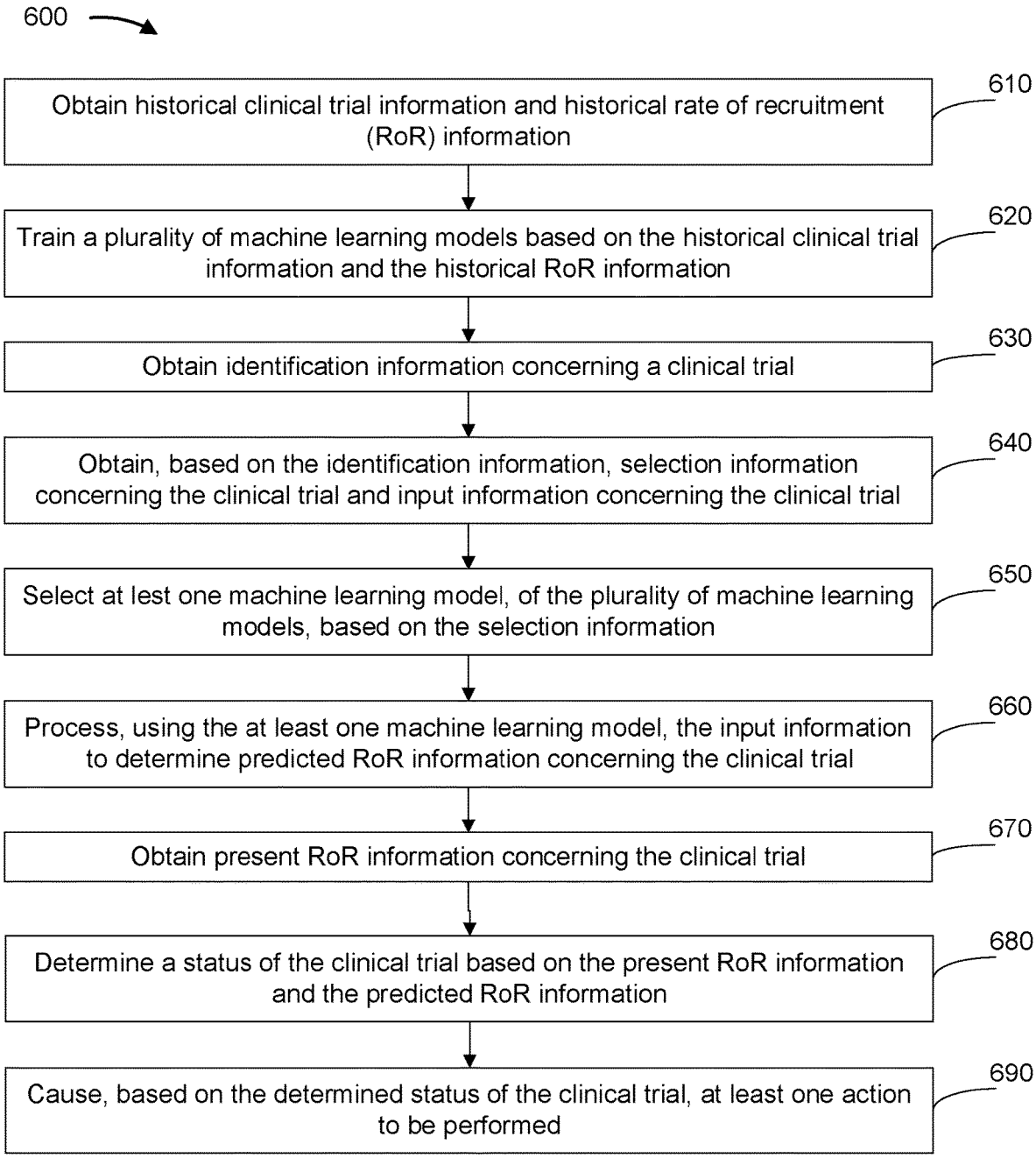

FIG. 6 is a flow chart of an example process 600 for determining rate of recruitment (RoR) information concerning a clinical trial. In some implementations, one or more process blocks of FIG. 6 may be performed by a prediction platform (e.g., prediction platform 220). In some implementations, one or more process blocks of FIG. 6 may be performed by another device or a group of devices separate from or including the prediction platform, such as a server device (e.g., server device 210), a client device (e.g., client device 230), and/or the like.

As shown in FIG. 6, process 600 may include obtaining historical clinical trial information and historical rate of recruitment (RoR) information (block 610). For example, the prediction platform (e.g., using computing resource 224, processor 320, memory 330, storage component 340, input component 350, output component 360, communication interface 370, and/or the like) may obtain historical clinical trial information and historical rate of recruitment (RoR) information, as described above.

As further shown in FIG. 6, process 600 may include training a plurality of machine learning models based on the historical clinical trial information and the historical RoR information (block 620). For example, the prediction platform (e.g., using computing resource 224, processor 320, memory 330, storage component 340, input component 350, output component 360, communication interface 370, and/or the like) may train a plurality of machine learning models based on the historical clinical trial information and the historical RoR information, as described above.

As further shown in FIG. 6, process 600 may include obtaining identification information concerning a clinical trial (block 630). For example, the prediction platform (e.g., using computing resource 224, processor 320, memory 330, storage component 340, input component 350, output component 360, communication interface 370, and/or the like) may obtain identification information concerning a clinical trial, as described above.

As further shown in FIG. 6, process 600 may include obtaining, based on the identification information, selection information concerning the clinical trial and input information concerning the clinical trial (block 640). For example, the prediction platform (e.g., using computing resource 224, processor 320, memory 330, storage component 340, input component 350, output component 360, communication interface 370, and/or the like) may obtain, based on the identification information, selection information concerning the clinical trial and input information concerning the clinical trial, as described above.

As further shown in FIG. 6, process 600 may include selecting at least one machine learning model, of the plurality of machine learning models, based on the selection information (block 650). For example, the prediction platform (e.g., using computing resource 224, processor 320, memory 330, storage component 340, input component 350, output component 360, communication interface 370, and/or the like) may select at least one machine learning model, of the plurality of machine learning models, based on the selection information, as described above.

As further shown in FIG. 6, process 600 may include processing, using the at least one machine learning model, the input information to determine predicted RoR information concerning the clinical trial (block 660). For example, the prediction platform (e.g., using computing resource 224, processor 320, memory 330, storage component 340, input component 350, output component 360, communication interface 370, and/or the like) may process, using the at least one machine learning model, the input information to determine predicted RoR information concerning the clinical trial, as described above.

As further shown in FIG. 6, process 600 may include obtaining present RoR information concerning the clinical trial (block 670). For example, the prediction platform (e.g., using computing resource 224, processor 320, memory 330, storage component 340, input component 350, output component 360, communication interface 370, and/or the like) may obtain present RoR information concerning the clinical trial, as described above.

As further shown in FIG. 6, process 600 may include determining a status of the clinical trial based on the present RoR information and the predicted RoR information (block 680). For example, the prediction platform (e.g., using computing resource 224, processor 320, memory 330, storage component 340, input component 350, output component 360, communication interface 370, and/or the like) may determine a status of the clinical trial based on the present RoR information and the predicted RoR information, as described above.

As further shown in FIG. 6, process 600 may include causing, based on the determined status of the clinical trial, at least one action to be performed (block 690). For example, the prediction platform (e.g., using computing resource 224, processor 320, memory 330, storage component 340, input component 350, output component 360, communication interface 370, and/or the like) may cause, based on the determined status of the clinical trial, at least one action to be performed, as described above.

Process 600 may include additional implementations, such as any single implementation or any combination of implementations described below and/or in connection with one or more other processes described elsewhere herein.

In a first implementation, the predicted RoR information may include at least one of: a plurality of predicted RoR values concerning the clinical trial; a plurality of predicted durations concerning the clinical trial, wherein each predicted duration, of the plurality of predicted durations, is associated with a respective predicted RoR value of the plurality of predicted RoR values; or a plurality of predicted numbers of sites associated with the clinical trial, wherein each predicted number of sites, of the plurality of predicted numbers of sites, is associated with a respective predicted RoR value of the plurality of predicted RoR values.

In a second implementation, alone or in combination with the first implementation, when determining the status of the clinical trial, the prediction platform may determine, based on the present RoR information, a present RoR value concerning the clinical trial; may determine, based on the predicted RoR information, a predicted RoR value concerning the clinical trial; may determine a difference between the present RoR value and the predicted RoR value; and may determine the status based on the difference.

In a third implementation, alone or in combination with one or more of the first and second implementations, when determining the status of the clinical trial, the prediction platform may determine, based on the present RoR information, an estimated duration of the clinical trial; may determine, based on the predicted RoR information, a predicted duration of the clinical trial; may determine a difference between the estimated duration and the predicted duration; and may determine the status based on the difference.

In a fourth implementation, alone or in combination with one or more of the first through third implementations, when causing the at least one action to be performed, the prediction platform may generate, based on the determined status, a message recommending that a duration of the clinical trial or a number of sites associated with the clinical trial should be changed, and may cause a different device to display the message on a display of the different device.

In a fifth implementation, alone or in combination with one or more of the first through fourth implementations, when training the plurality of machine learning models based on the historical clinical trial information and the historical RoR information, the prediction platform may process the historical clinical trial information and the historical RoR information, with one or more data processing techniques, to generate processed historical clinical trial information and processed historical RoR information; and may train the plurality of machine learning models with the processed historical clinical trial information and the processed historical RoR information.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, a dynamically generated configuration based on user input, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
    obtaining, by a device, historical clinical trial information and historical rate of recruitment (RoR) information,
        wherein the historical clinical trial information includes historical information concerning incidence and/or prevalence of a disease;
    preprocessing, by the device, the historical clinical trial information and the historical RoR information,
        wherein preprocessing the historical clinical trial information and the historical RoR information comprises removing confidential data in the historical clinical trial information and the historical RoR information;
    training, by the device, a plurality of machine learning models based on the historical clinical trial information and the historical RoR information;
    obtaining, by the device, identification information concerning a clinical trial,
        wherein the identification information includes information associated with a protocol that concerns the clinical trial;
    obtaining, by the device and based on the identification information, selection information concerning the clinical trial and input information concerning the clinical trial;
    selecting, by the device, at least one machine learning model, of the plurality of machine learning models, based on using at least one additional machine learning model and the selection information,
        wherein the at least one additional machine learning model is trained based on historical identification information and historical selection information to determine an association between the selection information and the at least one machine learning model, and
        wherein selecting the at least one machine learning model comprises:
            identifying the plurality of machine learning models,
            determining one or more elements based on the selection information and the identification information,
            processing the one or more elements,
                wherein processing the one or more elements comprises identifying a particular element, of the one or more elements, associated with a relationship of high predictive significance with the at least one machine learning model, and
            selecting the at least one machine learning model based on the particular element;
    processing, by the device and using the at least one machine learning model, the input information, the historical clinical trial information, the historical information concerning incidence and/or prevalence of the disease, and the information associated with the protocol that concerns the clinical trial;
    determining, by the device and based on processing the input information, the historical clinical trial information, the historical information concerning incidence and/or prevalence of the disease, and the information associated with the protocol that concerns the clinical trial, predicted RoR information concerning the clinical trial;
    obtaining, by the device, present RoR information concerning the clinical trial;
    determining, by the device, a status of the clinical trial based on the present RoR information and the predicted RoR information;
    selectively:
        displaying, by the device, a recommendation that a duration of the clinical trial be extended and/or a number of sites be increased when the status indicates that the clinical trial is underperforming, and
        displaying, by the device, a recommendation that the duration of the clinical trial be reduced and/or the number of sites be decreased when the status indicates that the clinical trial is overperforming;
    updating, by the device, the at least one machine learning model based on determining the status; and
    processing, by the device and using the at least one machine learning model after the at least one machine learning model has been updated, the present RoR information, the predicted RoR information, the status, and the input information.

2. The method of claim 1, further comprising:
    causing, by the device and based on the status of the clinical trial, at least one action to be performed.

3. The method of claim 2, wherein processing, using the at least one machine learning model after the at least one machine learning model has been updated, the present RoR information, the predicted RoR information, the status, and the input information, comprises:
    processing, using the at least one machine learning model after the at least one machine learning model has been updated, the present RoR information, the predicted RoR information, the status, or the input information to cause a predicted RoR value concerning the clinical trial of the RoR information to be updated.

4. The method of claim 1, wherein the identification information comprises at least one of:
    an identifier associated with the protocol that concerns the clinical trial;
    a version associated with the protocol;
    a phase associated with the protocol; or
    a title associated with the protocol.

5. The method of claim 1, wherein the selection information comprises at least one of:
    a total number of participants participating in the clinical trial;
    a total number of sites associated with the clinical trial;
    information identifying geographic areas associated with the clinical trial;
    information identifying and/or associated with one or more sites associated with the clinical trial;
    information concerning approval of the protocol associated with the clinical trial;

information concerning activation of a first site associated with the clinical trial;
information concerning a rarity of the disease;
information concerning a sponsor of the clinical trial;
information concerning a therapeutic area associated with the clinical trial; or
information concerning an indication associated with the clinical trial.

6. The method of claim 1, wherein the input information comprises at least one of:
information concerning an objective associated with the clinical trial;
information concerning a primary end point associated with the clinical trial;
information concerning an explicitly requested disease sub-type associated with the clinical trial;
information concerning a specific disease characteristic associated with the clinical trial;
information concerning a participant characteristic associated with the clinical trial;
information concerning a targeted indication associated with the clinical trial;
information concerning geographic areas associated with the clinical trial;
information concerning an initiator associated with the clinical trial;
information identifying a sponsor associated with the clinical trial
information concerning a procedure associated with the clinical trial;
information concerning inclusion and exclusion criteria associated with the clinical trial;
information concerning a therapeutic area associated with the clinical trial;
information concerning an indication associated with the clinical trial;
information concerning targeted participant population information associated with the clinical trial;
information concerning treatment arms associated with the clinical trial; or
information concerning design of the protocol associated with the clinical trial.

7. The method of claim 1, wherein the predicted RoR information comprises at least one of:
a predicted RoR value concerning the clinical trial;
a predicted duration of the clinical trial; or
a predicted number of sites associated with the clinical trial.

8. The method of claim 1, wherein selecting the at least one machine learning model comprises:
determining that the selection information comprises the one or more elements.

9. The method of claim 1, wherein processing the input information to determine the predicted RoR information comprises:
processing the input information to identify parameters that include key words, phrases, relationships, or concepts associated with the clinical trial; and
processing the parameters using the at least one machine learning model to determine the predicted RoR information.

10. A device, comprising:
one or more memories; and
one or more processors coupled to the one or more memories, to:
obtain historical clinical trial information and historical rate of recruitment (RoR) information;
preprocess the historical clinical trial information and the historical RoR information,
wherein the one or more processors, to preprocess the historical clinical trial information and the historical RoR information, are configured to remove confidential information from the historical clinical trial information and the historical RoR information;
train a plurality of machine learning models based on the historical clinical trial information and the historical RoR information;
obtain identification information concerning a clinical trial from a first different device,
wherein the identification information includes information associated with a protocol that concerns the clinical trial;
obtain, based on the identification information, selection information concerning the clinical trial and input information concerning the clinical trial from a second different device;
select at least one machine learning model, of the plurality of machine learning models, based on the identification information and the selection information,
wherein the one or more processors, to select the at least one machine learning model, are configured to:
identify the plurality of machine learning models,
determine one or more elements based on the selection information and the identification information,
process the one or more elements,
wherein the one or more processors, to process the one or more elements, are configured to identify a particular element, of the one or more elements, associated with a relationship of high predictive significance with the at least one machine learning model, and
select the at least one machine learning model based on the particular element;
process, using the at least one machine learning model, the input information, the historical clinical trial information, historical information concerning incidence and/or prevalence of a disease, and the information associated with the protocol that concerns the clinical trial;
determine, based on processing the input information, the historical clinical trial information, the historical information concerning incidence and/or prevalence of the disease, and the information associated with the protocol that concerns the clinical trial, predicted RoR information concerning the clinical trial;
obtain present RoR information concerning the clinical trial;
determine a status of the clinical trial based on the present RoR information and the predicted RoR information;
selectively:
display a recommendation that a duration of the clinical trial be extended and/or a number of sites be increased when the status indicates that the clinical trial is underperforming, and
display a recommendation that the duration of the clinical trial be reduced and/or the number of sites be decreased when the status indicates that the clinical trial is overperforming;
update the at least one machine learning model based on determining the status; and process, using the at least one machine learning model after the at least one machine learning model has been updated, the present RoR information, the predicted RoR information, the status, and the input information.

11. The device of claim 10, wherein the one or more processors, to select the at least one machine learning model, are to:
  process, using at least one additional machine learning model, the identification information and the selection information to select the at least one machine learning model.

12. The device of claim 10, wherein the one or more processors, to obtain the present RoR information concerning the clinical trial, are to:
  obtain the present RoR information concerning the clinical trial from the first different device,
    wherein the present RoR information includes one or more present RoR values that are each respectively associated with one or more criteria included in the selection information; and
  cause, based on the status of the clinical trial, at least one action to be performed.

13. The device of claim 12, wherein the one or more processors, to determine the status of the clinical trial, are to:
  determine, based on the present RoR information, the one or more present RoR values;
  determine, based on the predicted RoR information, the one or more predicted RoR values;
  determine, for each geographic area of one or more geographic areas, a difference between a present RoR value, of the one or more present RoR values, associated with the geographic area and a predicted RoR value, of the one or more predicted RoR values, associated with the geographic area; and
  determine the status based on the respective difference associated with each geographic area of the one or more geographic areas.

14. The device of claim 12, wherein the one or more processors, to cause the at least one action to be performed, are to:
  generate an alert concerning the status of the clinical trial; and
  cause a third different device to display the alert on a display of the third different device.

15. A non-transitory computer-readable medium storing instructions, the instructions comprising:
  one or more instructions that, when executed by one or more processors, cause the one or more processors to:
    obtain historical clinical trial information and historical rate of recruitment (RoR) information;
    preprocess the historical clinical trial information and the historical RoR information,
      wherein the one or more instructions, that cause the one or more processors to preprocess the historical clinical trial information and the historical RoR information, cause the one or more processors to remove confidential information from the historical clinical trial information and the historical RoR information;
    train a plurality of machine learning models based on the historical clinical trial information and the historical RoR information;
    obtain identification information concerning a clinical trial,
      wherein the identification information includes information associated with a protocol that concerns the clinical trial;
    obtain, based on the identification information, selection information concerning the clinical trial and input information concerning the clinical trial;
    select at least one machine learning model, of the plurality of machine learning models, based on the selection information,
      wherein the one or more instructions that cause the one or more processors to select the at least one machine learning model, cause the one or more processors to:
        identify the plurality of machine learning models,
        determine one or more elements based on the selection information and the identification information,
        process the one or more elements,
          wherein the one or more instructions, that cause the one or more processors to process the one or more elements, cause the one or more processors to identify a particular element, of the one or more elements, associated with a relationship of high predictive significance with the at least one machine learning model, and
        select the at least one machine learning model based on the particular element;
    process, using the at least one machine learning model, the input information, the historical clinical trial information, historical information concerning incidence and/or prevalence of a disease, and the information associated with the protocol that concerns the clinical trial;
    determine, based on processing the input information, the historical clinical trial information, the historical information concerning incidence and/or prevalence of the disease, and the information associated with the protocol that concerns the clinical trial, predicted RoR information concerning the clinical trial;
    obtain present RoR information concerning the clinical trial;
    determine a status of the clinical trial based on the present RoR information and the predicted RoR information;
    cause, based on the status of the clinical trial, at least one action to be performed;
      wherein the one or more instructions, that cause the one or more processors to cause the at least one action to be performed, cause the one or more processors to: selectively:
        display a recommendation that a duration of the clinical trial be extended and/or a number of sites be increased when the status indicates that the clinical trial is underperforming, and
        display a recommendation that the duration of the clinical trial be reduced and/or the number of sites be decreased when the status indicates that the clinical trial is overperforming;
    update the at least one machine learning model based on determining the status; and
    process, using the at least one machine learning model after the at least one machine learning model has been updated, the present RoR information, the predicted RoR information, the status, and the input information.

16. The non-transitory computer-readable medium of claim 15, wherein the predicted RoR information includes at least one of:
  a plurality of predicted RoR values concerning the clinical trial;
  a plurality of predicted durations concerning the clinical trial, wherein each predicted duration, of the plurality of predicted durations, is associated with a respective predicted RoR value of the plurality of predicted RoR values; or a plurality of predicted numbers of sites associated with the clinical trial, wherein each predicted number of sites, of the plurality of predicted numbers of sites, is associated with a respective predicted RoR value of the plurality of predicted RoR values.

17. The non-transitory computer-readable medium of claim 15, wherein the one or more instructions, that cause the one or more processors to determine the status of the clinical trial, cause the one or more processors to:

determine, based on the present RoR information, a present RoR value concerning the clinical trial;

determine, based on the predicted RoR information, a predicted RoR value concerning the clinical trial;

determine a difference between the present RoR value and the predicted RoR value; and determine the status based on the difference.

18. The non-transitory computer-readable medium of claim 15, wherein the one or more instructions, that cause the one or more processors to determine the status of the clinical trial, cause the one or more processors to:

determine, based on the present RoR information, an estimated duration of the clinical trial;

determine, based on the predicted RoR information, a predicted duration of the clinical trial;

determine a difference between the estimated duration and the predicted duration; and determine the status based on the difference.

19. The non-transitory computer-readable medium of claim 15, wherein the one or more instructions, that cause the one or more processors to display the recommendation that the duration of the clinical trial be extended and/or the number of sites be increased when the status indicates that the clinical trial is underperforming and display the recommendation that the duration of the clinical trial be reduced and/or the number of sites be decreased when the status indicates that the clinical trial is overperforming, cause the one or more processors to:

generate a message recommending that the duration of the clinical trial or the number of sites associated with the clinical trial should be changed; and cause a different device to display the message on a display of the different device.

20. The non-transitory computer-readable medium of claim 15, wherein the one or more instructions, that cause the one or more processors to train the plurality of machine learning models based on the historical clinical trial information and the historical RoR information, cause the one or more processors to:

process the historical clinical trial information and the historical RoR information, with one or more data processing techniques, to generate processed historical clinical trial information and processed historical RoR information; and train the plurality of machine learning models with the processed historical clinical trial information and the processed historical RoR information.

* * * * *